United States Patent [19]

Francotte

[11] Patent Number: 5,684,199
[45] Date of Patent: Nov. 4, 1997

US005684199A

[54] PROCESS FOR THE PREPARATION OF AN OPTICALLY PURE ENANTIOMER OF FORMOTEROL

[75] Inventor: Eric Francotte, Nuglar, Switzerland

[73] Assignee: Novartis Corporation, Summit, N.J.

[21] Appl. No.: 663,143
[22] PCT Filed: Dec. 16, 1996
[86] PCT No.: PCT/EP94/04199
 § 371 Date: Jun. 13, 1996
 § 102(e) Date: Jun. 13, 1996
[87] PCT Pub. No.: WO95/18094
 PCT Pub. Date: Jul. 6, 1995

[30] Foreign Application Priority Data

Dec. 28, 1993 [CH] Switzerland ............. 3875/93

[51] Int. Cl.$^6$ ............. C07C 231/20; C07C 233/43
[52] U.S. Cl. ............. 564/216; 564/220
[58] Field of Search ............. 564/216, 220

[56] References Cited

FOREIGN PATENT DOCUMENTS 9205147 4/1992 WIPO .

OTHER PUBLICATIONS

Murase et al., Chem. Pharm. Bull. 26(4) 1123–1129 (1978).

Primary Examiner—Richard L. Raymond
Attorney, Agent, or Firm—Gregory D. Ferraro

[57] ABSTRACT

The present invention is directed to a process for preparing formoterol and related compounds and derivatives thereof and their pharmacologically and pharmaceutically acceptable fumarate salts and/or solvates. The present invention is also directed to certain formoterol related compounds per se.

7 Claims, No Drawings

PROCESS FOR THE PREPARATION OF AN OPTICALLY PURE ENANTIOMER OF FORMOTEROL

This is a 371 of PCT/EP94/04199, filed Dec. 16, 1994.

The present invention relates to a novel useful process for the preparation of the optically pure R,R-enantiomer of formoterol. Formoterol: N-[2-hydroxy-5-(1-hydroxy-2-((2-4-methoxyphenyl)-1-methylethyl)amino)ethyl)phenyl] formamide and the fumarate salt of this compound, q.v. Merck Index, Eleventh Edition No. 4159, belongs to the group of the selective $\beta_2$-sympathomimetic bronchodilutors which are useful antiasthmatic drugs. Preferred suitable dosage forms are aerosols for inhalation. A known commercial product in aerosol formulation for inhalation is ®Foradil (Ciba), which is available in numerous countries.

The pair of (R,R),(S,S)-enantiomers of formoterol and their separation into two optically pure enantiomers and two diastereisomers are described in Chem. Pharm. Bull. 26, No.4, 1123–1129 (1978). Chirality 3:443–450 (1991) describes the enhanced activity of the R,R-enantiomer over the S,S-enantiomer. It is generally assumed of chiral beta-sympathomimetics that only one optically pure antipode of a pair of enantiomers is active. The other antipode of the pair of enantiomers is either inactive or may even cause side-effects, q.v. in this connection TIPS, June 1992 [Vol. 13], pp. 231–232. The preparation of the R,R-enantiomer in high optical purity is carried out, in poor yield, by a number of complicated, and therefore expensive, synthesis steps using chiral starting materials and intermediates.

It is the object of this invention to provide a simplified, improved, and therefore more cost-effective, process for the preparation of the R,R-enantiomer of the free base of formoterol in increased yield and, in particular, in high purity of optically pure product.

Surprisingly, this object is achieved by this invention, which relates to a process for the preparation of optically pure (R,R)-N-[2-hydroxy-5-(1-hydroxy-2-((2-(4-methoxyphenyl)-1-methylethyl)amino)ethyl)phenyl] formamide and the fumarate salt thereof. The process comprises separating the racemic mixture or mixture of diastereoisomers of the free compound in a mobile phase containing a nonpolar solvent and optionally a further polar protic or aprotic solvent by chromatography on a chiral stationary phase consisting of a polysaccharide whose free hydroxyl groups are derivatised by the 4-methylbenzoyl group, and optionally an inert carrier material, and isolating the optically pure R,R compound from the eluate of the mobile phase and convening said compound into the fumarate salt.

An essential advantage of this process resides in its combination with known cost-effective methods of preparing racemic formoterol. Racemic formoterol is prepared in per se known manner and then subjected to the novel chromatographic separation method. In one process step, the racereit mixture of formoterol is separated into the optically pure enantiomers. No troublesome synthesis of optically pure intermediates is necessary.

The terms used in the description of this invention are preferably defined as follows.

The term "optically pure" denotes in respect of a defined compound having at least one centre of chirality that said compound contains more than 95% by weight, preferably more than 99% by weight, most preferably more than 99.9% by weight, of an antipode with defined configuration, e.g. according to the known rules of sequencing of Kahn, Ingold and Prelog.

The term "racemic mixture" denotes in respect of a defined compound having at least one centre of chirality a c. 1: mixture of two antipodes with defined configuration.

The term "mixture of diastereoisomers" denotes in respect of a defined compound having at least two centres of chirality a defined configuration with regard to one centre of chirality, whereas the configuration with regard to the further centre of chirality is racemic.

The term "mobile phase" defines a solvent or mixture of solvents in which the racemic mixture for separation into the optically pure antipodes, or a mixture of diastereoisomers of formoterol, is dissolved. However, an inert gas, conveniently argon, may also be used as mobile phase if the method of preparative gas chromatography is applied.

Suitable solvents for the mobile phase are mixtures of a nonpolar solvent with a polar protic or aprotic solvent.

Typical examples of nonpolar solvents are n-pentane, isooctane, petroleum ether, n-hexane, n-heptane, cyclohexane, cyclopentane, diisopropyl ether, cyclohexene, dimethoxyethane, or diethyl ether.

Typical examples of polar, protic or aprotic solvents are amyl alcohol, acetonitrile, isopropanol, n-propanol, n- or tert-butanol, ethanol, methanol, ethylene glycol, acetic acid or water.

It is preferred to use mixtures of a nonpolar solvent such as n-pentane, isooctane, petroleum ether, n-hexane, n-heptane, cyclohexane or cyclopentane, with a polar, protic solvent such as isopropanol or ethanol.

Mixtures of n-hexane or n-heptane with ethanol or n-hexane or n-heptane with n-isopropanol are particularly preferred.

The term "chromatographic separation" defines known methods of separating mixtures of substances which are dissolved in the mobile phase. Absorption or chemical reaction on a stationary phase establishes an equilibrium for the particular substance that causes characteristic retention times for the substance to be separated from the mixture.

Suitable known methods of chromatographic separation are typically adsorption chromatography, e.g. column chromatography or adsorption chromatography on adsorber resins, paper chromatography, thin-layer chromatography or preparative gas chromatography.

Particularly preferred separation methods are those known as HPLC (high performance liquid chromatography), and SMBA (simulated moving bed adsorption). These methods comprise using a chiral stationary phase, which consists of a polysaccharide whose free hydroxyl groups are derivatised by the 4-methylbenzoyl group. An inert carrier material can be coated with this polysaccharide.

A suitable inert carrier material for the chiral stationary phase is preferably macroporous, e.g. crosslinked polystyrene, polyacrylamide, polyacrylate, quartz, kieselgur, alumina, aluminosilicate xerogels, acidic magnesium silicate, magnesium oxide, titanium dioxide or kaolin. Silica gel is preferred.

The granular size of the inert carrier material can vary over a wide range and is typically from c. 1 μm to 1 mm, preferably from c. 1 to 300 μm. This material is porous with an average pore width of c. $1.0 \times 10^{-8}$ m to $1.0 \times 10^{-6}$ m.

The inert carrier material is coated with the derivatised polysaccharide in per se known manner, conveniently by treating the inert carrier, typically macroporous silica gel, with a solution of the derivatised polysaccharide in an organic solvent, e.g. ethanol or a mixture of methylene chloride-tetrahydrofuran, and evaporating the solvent. Numerous other methods are also known, including treatment in a fluidised-bed reactor, spraying, precipitation and the like. The macroporous silica gel can be activated beforehand by reaction with 3-aminopropyltriethoxysilane, dissolved in benzene.

The polysaccharide can be derivatised by reaction with 4-methylbenzoyl chloride. Cellulose of the ®Avicel type (Merck) is particularly suitable.

Derivatisable polysaccharides are optically active, natural or chemically modified polysaccharides, typically microcrystalline or native cellulose, cotton linters or cellulose from plant fibres such as cotton, flax, hemp, jute or ramie fibres.

The polysaccharide, preferably cellulose, is derivatised at 1–3, preferably 3, free hydroxyl groups by the 4-methylbenzoyl group, and can be used as coating agent for an inert carrier material or is itself used in the form of beads, q.v. published European patent application 186 133.

Suitable materials for the chiral stationary phase are known and commercially available, especially the commercial product ®Chiralcel (Daicel) OJ, which consists of silica gel that is coated with esterified cellulose. The ester group is the 4-methylbenzoyl group.

Particularly suitable columns for chromatographic separation by HPLC are those for electing separations on a semipreparative or preparative scale, e.g. having a diameter of 1–10 cm and a length of 20–60 cm. Particularly suitable average particle sizes of the carrier material are 10–20 µm for HPLC and 10–60 µm for SMBA.

The conversion of the free compound into its fumarate salt is carried out, if desired, in per se known manner by conventional reaction of the free compound with fumaric acid, or reaction of a sodium or potassium salt with fumaric acid or the acid chloride thereof.

The invention is illustrated by the following Examples.

EXAMPLE 1

2 g of a 2.5% solution of racemic formoterol in hexane/ethanol (85:15 vol %) are given to a chiral CHIRALCEL OJ (Daleel Chem.Ind., Japan) HPLC column (10×50 cm, granular size 20 µm). The carrier material consists of silica gel coated with p-methylbenzoyl cellulose. At a flow rate of c. 150 ml/min. and using hexane/ethanol (85:15 vol %) as mobile phase, the enantiomers are separated with a separation factor of α=1.54 as follows:

Optically pure fractions are obtained from 2 g of racemate and concentrated, affording 0.9 g of the first eluted anantiomer in an optical purity of ≧99.9%, and 1.15 g of the second eluted enantiomer in an optical purity of ≧98%. The fractions enriched with the second eluted enantiomer are chromatographed further until the optical purity is at least 99.5%. Both fractions are additionally purified by flash chromatography. Purification is effected on silica gel (34 g, granular size 40–63 µm, glass column 2.5×30 cm) in succession with mixtures of a) 250 ml of hexane/ethanol (2:1 parts by volume), b) 250 ml of hexane/ethanol (1:3 parts by volume) and c) 250 ml of hexane/ethanol (1:6 parts by volume) as mobile phases at a pressure of c. 0.2 bar. The purified fractions of the respective enantiomer are collected and then concentrated. Afterwards each residue is suspended in ether, concentrated once more and dried. The first enantiomer (0.730 g) and the second enantiomer (0.780 g) are each isolated in the form of a white powder.

To test the biological activity, each enantiomer is convened into its respective fumarate salt This is done by dissolving 1.72 g of each optically pure enantiomer in 10 ml of methanol and adding to the solution an equimolar amount (0.29 g) of fumaric acid. After a reaction time of 1 hour at room temperature, the clear solution is concentrated at 40° C. on a rotary evaporator and then dried at 40° C. for 6 hours under a high vacuum. The fumarate salts are isolated as hemifumarate monohydrates and characterised:

a) first eluted optically pure enantiomer: (−)-(R,R)-formoterol: $[\alpha]_D = -44.7 \pm 2.3°$;

b) second eluted optically pure enantiomer: (+)-(S,S)-formoterol: $[\alpha]_D = +47.0 \pm 0.2°$.

EXAMPLE 2

Separation of enantiomers of formoterol by simulated moving bed adsorption.

CONFIGURATION OF THE SYSTEM

System: Prep-SMB-System L, supplied by UOP (Universal Oil Products, Des Plaines Ill. 60017–5017, USA).

Column: 16 column (bed) system in rotary arrangement. Each column has an internal diameter of 16 mm and a length of 60 mm. The columns (vol. 0.193 ml) are filled by the slurry method. Chiral carrier material: Chiralcel® OJ, 20 µm; mobile phase: heptane-ethanol 70:30.

Separation

At a concentration of the racemate solution of 0.25% in heptane-ethanol 70:30; a flow rate of the racemate solution of 0,52 ml/min; a flow rate of the mobile phase of 6.69 ml/mm; a cycle time of 90 min; an extract rate of 3.59 ml/min; a raffinate rate of 3.62 ml/min, a productivity of 0.44 g per hour and per kg of chiral stationary phase is achieved for each enantiomer. The optical purity is 100% for the raffinate (RR enantiomer) and 97.4% for the extract (SS enantiomer).

What is claimed is:

1. A process for the preparation of optically pure (R,R)-N-[2-hydroxy-5-(1-hydroxy-2-((2-(4-methoxyphenyl)-1-methylethyl)amino)ethyl)phenyl]formamide or the fumarate salt thereof, which process comprises separating the recemic mixture or mixture of diastereoisomers of the free compound in a mobile phase containing a nonpolar solvent and optionally a further polar protic or aprotic solvent by chromatography on a chiral stationary phase consisting of a polysaccharide whose free hydroxyl groups are derivatised by the 4-methylbenzoyl group, and an inert carrier material, and isolating the optically pure R,R compound from the eluate of the mobile phase and convening said compound into the fumarate salt.

2. A process according to claim 1, which comprises separating a racemic mixture of the fumarate salt of N-[2-hydroxy-5-(1-hydroxy-2-((2-(4-methoxyphenyl)-1-methylethyl)-amino)ethyl)phenyl]formamide by chromatography.

3. A process according to claim 2, which comprises separating a racemic mixture of the fumarate salt of N-[2-hydroxy-5-(1-hydroxy-2-((2-(4-methoxyphenyl)-1-methylethyl)amino)ethyl)phenyl]formamide by HLPC.

4. A process according to claim 2, which comprises separating a racemic mixture of the fumarate salt of N-[2-hydroxy-5-(1-hydroxy-2-((2-(4-methoxyphenyl)-1-methylethyl)amino)ethyl)phenyl]formamide by SMBA.

5. A process according to claim 3, which comprises separating the racemic mixture in a mobile phase containing hexane or n-heptane as nonpolar solvent and ethanol as polar protic solvent.

6. A process according to claim 3, which comprises separating the racemic mixture by chromatography on a stationary phase consisting of silica gel as inert carrier coated with cellulose as polysaccharide which is derivatised by the 4-methylbenzoyl group.

7. A process according to claim 4, which comprises separating the racemic mixture in a mobile phase containing hexane or n-heptane as nonpolar solvent and ethanol as polar protic solvent.

* * * * *